(12) United States Patent
Pichler et al.

(10) Patent No.: US 9,260,389 B2
(45) Date of Patent: Feb. 16, 2016

(54) CRYSTAL FORMS OF SAXAGLIPTIN

(71) Applicants: Arthur Pichler, Kundl (AT); Josef Wieser, Kundl (AT); Christoph Langes, Kundl (AT); Milica Vukicevic, Kundl (AT)

(72) Inventors: Arthur Pichler, Kundl (AT); Josef Wieser, Kundl (AT); Christoph Langes, Kundl (AT); Milica Vukicevic, Kundl (AT)

(73) Assignee: SANDOZ AG, Basel (CH)

( * ) Notice: Subject to any disclaimer, the term of this patent is extended or adjusted under 35 U.S.C. 154(b) by 0 days.

(21) Appl. No.: 14/044,204

(22) Filed: Oct. 2, 2013

(65) Prior Publication Data

US 2014/0200252 A1  Jul. 17, 2014

Related U.S. Application Data

(62) Division of application No. 13/262,652, filed as application No. PCT/EP2010/054692 on Apr. 9, 2010, now abandoned.

(60) Provisional application No. 61/167,918, filed on Apr. 9, 2009.

(30) Foreign Application Priority Data

Apr. 9, 2009 (EP) .................................. 09157723
Nov. 6, 2009 (EP) .................................. 09175259

(51) Int. Cl.
*C07D 209/52* (2006.01)
*A61K 31/403* (2006.01)
*A61K 45/06* (2006.01)

(52) U.S. Cl.
CPC ............ *C07D 209/52* (2013.01); *A61K 31/403* (2013.01); *A61K 45/06* (2013.01)

(58) Field of Classification Search
CPC ............................ C07D 209/52; A61K 31/403
See application file for complete search history.

(56) References Cited

U.S. PATENT DOCUMENTS 6,395,767 B2    5/2002   Robl
2005/0266080 A1  12/2005  Desai
2009/0054303 A1   2/2009  Gougoutas

FOREIGN PATENT DOCUMENTS

WO    2008131149 A2   10/2008

OTHER PUBLICATIONS

Brittain (Polymorphism in Pharmaceutical Solids, vol. 95, 1999, Taylor & Francis, Harry G. Brittain (Ed.), 427 pp.).*
Morissette et al. (Advanced Drug Delivery Reviews 56 (2004) 275-300).*
Hurst et al., Analytica Chimica Acta, 337 (1997), 233-52.*
Campbell Roberts et al., J. Pharm. Biomed. Anal., 28 (2002) 1149-59.*
Chen et al., J. Pharm. Sci., (1999), v. 88, p. 1191-1200.*
Tiwari et al., J. Pharm. Biomed. Anal., 43 (2007) 865-72.*
International Search Report and Written Opinion (mailed Jul. 23, 2010).
Caira M.R., Crystalline Polymorphism of Organic Compounds, Topics in Current Chemistry, Springer Berlin, vol. 198, Jan. 1, 1998, pp. 165-166.
Hilfiker, Polymorphism in the Pharmaceutical Industry, Wiley-VCH 2006.
Brittain (Polymorphism in Pharmaceutical Solids, vol. 95., 1999, Taylor & Francis, Harry G. Brittain (Ed.), 427 pp.).
Morissette et. al. (Advanced Drug Delivery Reviews 56 (2004) 275-300).

* cited by examiner

*Primary Examiner* — Robert Havlin
(74) *Attorney, Agent, or Firm* — Jeffrey S. Melcher; Manelli Selter PLLC (57) ABSTRACT

The present invention relates to novel polymorphic forms of Saxagliptin Hydrochloride. The present invention also relates to methods of making polymorphic forms of Saxagliptin Hydrochloride.

8 Claims, 11 Drawing Sheets

CRYSTAL FORMS OF SAXAGLIPTIN

The present invention relates to novel polymorphic forms of Saxagliptin Hydrochloride, their preparation and compositions containing them.

Saxagliptin(1S,3S,5S)-2-[(2S)-2-amino-2-(3-hydroxy-1-adamantyl)acetyl]-2-azabicyclo[3.1.0]hexane-3-carbonitrile or its hydrochloride salt is an orally active reversible dipeptidyl peptidase-4 (DD4) inhibitor, which is a therapeutic agent for treatment of type-2 diabetes mellitus, obesity or related diseases, and is disclosed for example in U.S. Pat. No. 6,395,767 B2, example 60.

Certain crystal forms of Saxagliptin and certain acid addition salts including Saxagliptin Hydrochloride are disclosed in WO 2008131149 A2. The occurrence of different crystalline forms of a single compound is known as polymorphism and is a property of some compounds and complexes and pseudopolymorphs. Polymorphic forms each have distinct physical properties, such as a distinct solubility profile, different melting point and/or different x-ray diffraction peaks.

Since the solubility of each polymorph may vary, identifying the existence of pharmaceutical polymorphs is important for providing pharmaceutical compositions with predictable solubility profiles. It is desirable to investigate all solid state forms of a drug, including all polymorphic forms, pseudopolymorphs and hydrates, and to determine the stability, dissolution and flow properties of each polymorphic form. For a general review of polymorphs and the relevance of solid state properties for pharmaceutical products see e.g. Rolf Hilfiker, Polymorphism in the Pharmaceutical industry, Wiley-VCH 2006.

The discovery of new polymorphic forms of a pharmaceutically useful compound provides a new opportunity to improve the performance characteristics of a pharmaceutical product. It enlarges the repertoire of materials that a formulation scientist has available for designing, for example, a pharmaceutical dosage form of a drug with a targeted release profile or other desired characteristic.

The known polymorphic forms of Saxagliptin hydrochloride are all hydrated forms having a relatively high water content. High-water content forms have certain drawbacks, as a compound prone to hydrolysis like Saxagliptin can show decreased chemical stability when present in such forms. Moreover, from a galenical perspective, bulk quantities of active pharmaceutical ingredients having a high water content tend to clog or stick together, thus sometimes having poor processing behavior in the formulation processes for the production of pharmaceutical compositions.

There is thus a need for solid forms of Saxagliptin hydrochloride which avoid one or more problems of the known crystal forms.

In accordance with the present invention new anhydrous forms of Saxagliptin Hydrochloride preferably of the formula are provided having a water content of not more than 1.5% w/w preferably in substantially pure form as
a) an anhydrous form designated as Form I-S
b) an anhydrous form designated as form HT-S
c) an anhydrous form designated as form HT-IV-S
d) an anhydrous form designated as form IV-S.

The water content is determined according to the Karl Fischer method.

An anhydrous form of Saxagliptin hydrochloride in the context of the present invention is defined as a form of Saxagliptin hydrochloride which, after storage at 30% relative humidity at 25° C. for 24 hours shows a water content of not more than 1.5% w/w according to the Karl Fischer method.

DETAILED DESCRIPTION

The Saxagliptin hydrochloride used as educt is one of the known forms containing water, e.g. forms H2-1, H1.25-2 or H.75-3 as identified in WO 2008/131149 A2 on page 2.

Form I-S

In a first aspect the present invention provides a crystalline form of Saxagliptin hydrochloride, designated as form I-S, which can be characterized by x-ray powder diffraction reflections at about 6.7, 14.6, 15.2, 16.6 and 17, 9±0.2 degrees two-theta, in particular comprising further peaks at about 13.5, 24.5 and 28.1. Form I S of Saxagliptin can be further characterized by a PXRD pattern substantially in accordance with FIG. 1.

Alternatively crystalline form I-S of Saxagliptin hydrochloride can be described by an infrared spectrum comprising peaks at wavenumbers of 2907, 2853, 1637, 1589, 1462, 1391, 1318, 1045, 1014 and 775+/−2 cm-1. Form I S of Saxagliptin hydrochloride can be further characterized by an FTTR spectrum substantially in accordance with FIG. 2.

Anhydrous crystalline Saxagliptin hydrochloride in the form of form I-S can be prepared by crystallization of Saxagliptin hydrochloride from an alcohol, preferably ethanol in the presence of seeds of from I-S, for example as described in example 2. Seeds of from I-S were surprisingly obtained by dissolving Saxagliptin free base hemihydrate in an organic solvent, precipitation with an alkyl halide dihydrate, removing precipitated Saxagliptin monohydrochloride dehydrate and crystallizing from the mother liquor after cooling, see example 1. Crystalline Saxagliptin hydrochloride form I-S is a particularly preferred crystal form due to its high chemical stability combined with its high dissolution rate.

Form HT-S

In a second aspect the present invention provides a crystalline form of Saxagliptin hydrochloride, designated as form HT-S, which can be characterized by x-ray powder diffraction reflections at about 6.6, 11.5, 13.3, 16.7 and 17.6±0.2 degrees two-theta, in particular comprising further peaks at about 11.5 and 15.3. Form HT-S of Saxagliptin can be further characterized by a PXRD pattern substantially in accordance with FIG. 4.

Alternatively crystalline form HT-S of Saxagliptin hydrochloride can be described by an infrared spectrum comprising peaks at wavenumbers of 2906, 2854, 1649, 1574, 1513, 1459, 1338, 1124, 1032 and 851+/−2 cm-1. Form HT-S of Saxagliptin hydrochloride can be further characterized by an FTIR spectrum substantially in accordance with FIG. 5.

The crystalline Saxagliptin hydrochloride in the form of HT-S can be prepared by heating known forms Saxagliptin hydrochloride to about 160° C. to 180° C. and isolating form HT-S. In particular, form HT-S may be prepared as described in example 3.

Form HT-IV-S

In a third aspect the present invention provides a crystalline form of Saxagliptin hydrochloride, designated as form HT-IV-S, which can be characterized by x-ray powder diffraction reflections at about 2.6, 4.5, 6.8, 14.6 and 18.1±0.2 degrees two-theta. Form HT-IV-S of Saxagliptin can be further characterized by a PXRD pattern substantially in accordance with FIG. 7.

Alternatively crystalline form HT-IV-S of Saxagliptin hydrochloride can be described by an infrared spectrum comprising peaks at wavenumbers of 3495, 2921, 1637, 1616, 1464, 1242, 1103, 1013, 940 and 774+/−2 cm-1. Form HT-IV-S of Saxagliptin hydrochloride can be further characterized by an FTIR spectrum substantially in accordance with FIG. 8.

The crystalline Saxagliptin hydrochloride in the form HT-IV-S can be prepared by removing bound solvent from Saxagliptin-IV-S. In particular the form HT-IV-S can be obtained by drying the form IV-S described below in vacuo, e.g. at ambient temperature to about 100° C., e.g. at about 80° C.±10° C. for several hours, e.g. for 3 to 24 hours. In particular form HT-IV-S may be prepared as described in example 4. In one preferred embodiment Saxagliptin hydrochloride form HT-IV-S is prepared in a process comprising the steps of
a) dissolving Saxagliptin monohydrochloride in n-butanole,
b) removing n-butanole under reduced pressure to obtain a residue,
c) adding 2-methyl-2-butanol to obtain a slurry,
d) allowing a solvated crystalline form of Saxagliptin hydrochloride to form in the slurry,
e) removing the solvated crystalline form from the slurry, and
f) drying the solvated crystalline form obtained from step e) to obtain the anhydrous crystalline Saxagliptin hydrochloride form HT-IVs. Drying in step f) is preferably carried out at 80° C.+/−10° C. for 3-24 hours.

Form IV-S

Saxagliptin form IV-S can be characterized by x-ray powder diffraction reflections at about 2.4, 4.1, 4.7, 6.3 and 15, 6±0.2 degrees two-theta. Form IV-S of Saxagliptin can be further characterized by a PXRD pattern substantially in accordance with FIG. 1. The crystalline Saxagliptin hydrochloride in the form of form IV-S can be, and preferably is prepared by crystallisation of Saxagliptin hydrochloride from tert. Amylalkohol (2-methyl-2-butanol) as described in example 5. A solution of Saxagliptin Hydrochloride in n-butanole is evaporated to dryness to produce an amorphous or weakly crystalline residue. Upon suspending the residue in tert.amylalkohol the novel crystalline form IV-S of Saxaglipin Hydrochloride is formed, which is a tert.amylcohol solvate of Saxagliptin hydrochloride.

Saxagliptin hydrochloride form IV-S is a valuable intermediate in the preparation of Saxagliptin hydrochloride form HT-TV-S.

Most preferably the solution of Saxagliptin hydrochloride is prepared using known form Dihydrate H2.1. The crystals are then isolated and kept at a relative humidity of less than to about 40%.

Pharmaceutical Formulations and Compositions

Any one of the crystal forms of Saxagliptin Hydrochloride of the invention as described above may be employed in various pharmaceutical formulations for use in treating diabetes and related diseases in accordance with the present invention. The present invention therefore also relates to a pharmaceutical composition which includes any one of the crystalline forms of saxagliptin hydrochloride as described above and a pharmaceutically acceptable carrier.

The novel crystal forms of Saxagliptin Hydrochloride may be used alone or in combination with one or more types of antidiabetic agents (employed to treat diabetes and related diseases) and/or one or more other types of therapeutic agents which may be administered orally in the same dosage form, in a separate dosage form or by injection.

The other types of antidiabetic agent which may optionally be employed in combination with the novel crystal forms of the compound of formula I are further antidiabetic agents or antihyperglycemic, hypolipidemic or lipid-modulating agents including insulin secretagogues or other antidiabetic agents preferably having a mechanism different from DP4 inhibition and may include biguanidines, sulfonyl ureas, glucosidase inhibitors, PPAR γ agonists, such as thiazolidinediones, SGLT2 inhibitors, PAR α/γ dual antagonists, aP" inhibitors, glycogen phosphorylase inhibitors, and/or meglitinides, as well as insulin and/or glucagons-like peptide-1 (GLP-1) or mimetics thereof.

The present invention also relates to a pharmaceutical composition containing the novel crystalline forms form I-S, form HT-S, form HT-IV or form IV-S of the compound of formula I, with or without another antidiabetic agent and/or other therapeutic agent, in association with a pharmaceutical vehicle or diluent. The pharmaceutical composition can be formulated employing conventional solid or liquid vehicles or diluents and pharmaceutical additives of a type appropriate to the mode of desired administration. For example, for the administration by an oral route the pharmaceutical composition of the invention may be in the form of tablets, capsules, granules or powders. The dose for adults is preferably between 5 mg to 1000 mg per day, preferably between 5 and 100 mg per day, which can be administered in a single dose or in the individual doses from 1-4 times a day.

The pharmaceutical compositions of the invention comprising the crystalline form of Saxagliptin hydrochloride according to the present invention may further comprise one or more pharmaceutically acceptable excipients which are preferably selected from the group consisting of fillers, sweeteners, buffering agents, glidants, flowing agents, flavoring agents, lubricants, preservatives, surfactants, wetting agents, binders, disintegrants and thickeners. Other excipients known in the field of pharmaceutical compositions may also be used. Furthermore, the pharmaceutical compositions may comprise a combination of 2 or more excipients also within one of the members of the above mentioned group. Preferably, the fillers are also sweeteners.

A typical tablet contains a one or more excipients such as bulking agents, optionally a binder and optionally a disintegrant. Examples of bulking agents include cellulose derivatives, such as microcrystalline cellulose, lactose, sucrose, starch, pregelatinized starch, dextrose, mannitol, fructose, xylitol, sorbitol, corn starch, inorganic salts such as calcium salts, e.g. calcium carbonate, calcium phosphate, dicalcium phosphate, dextrin or dextrates, maltodextrin compressable sugars and/or other known bulking agents or fillers.

Examples of binders suitable for use include hydroxypropylcellulose, PVP, starch, hydroxypropylcellulose, cellulose acetate as well as a wax binder such as carnauba wax, polyethylenes or other conventional binding agents or mixtures thereof.

Examples of disintegrants include croscarmellose sodium, crospovidone, starch, low substituted hydroxypropyl cellulose as well as other conventional desintegrants.

The lubricant optionally present include for example magnesium stearate, zinc stearate, calcium stearate, talc, carnauba wax, stearic acid, palmitinic acid, sodium laurylsulfate or hydrogenated vegetable oils and fats or other known lubricats or mixtures thereof.

Tablets may be coated including a tablet core and a inner seal coating layer coated on the tablet core, a second coating layer containing the crystals of the present invention coated on the inner seal coating on the tablet core and optionally an outer protective coating layer coated on the second coating layer of the tablet as e.g. disclosed in US 2005/0266080.

The present invention therefore also provides such coated tablets as described in sections to section [0073] of US 2005/0266080 A1, where it is to be understood that whenever US 2005/0266080 A1 is using the term "medicament", the crystalline saxagliptin hydrochloride of the present invention is to be used instead of the "medicament" of US 2005/0266080 A1. It goes without saying that especially when form I-S, form IV-S or form HT-IV-s is used, all steps are typically carried out under such conditions which avoid polymorphic transformation, such as conditions of relatively low relative humidity.

Typical capsules for oral administration containing the novel crystalline forms of the invention contain e.g, lactose, crosscarmelose, magnesium stearate or e.g. sodium stearyl fumararte.

Purity

The present inventors have found ways to stabilize especially form I-S, form HT-IV-S and form IV-S during the formulation and storage process.

The present invention therefore also relates to a pharmaceutical composition comprising the crystalline form of Saxagliptin hydrochloride designated as form 1-S, wherein more than 95% of the crystalline form of Saxagliptin hydrochloride, designated as form I-S, present in said composition is stably present as form I-S, in particular, the present invention relates to such pharmaceutical compositions wherein form I-S is the only detectable crystalline from of Saxagliptin hydrochloride.

The present invention therefore also relates to a pharmaceutical composition comprising the crystalline form of Saxagliptin hydrochloride designated as form HT-IV-S, wherein more than 95% of the crystalline form of Saxagliptin hydrochloride, designated as form HT-IV-S, present in said composition is stably present as form HT-IV-S, in particular, the present invention relates to such pharmaceutical compositions wherein form HT-IV-S is the only detectable crystalline from of Saxagliptin hydrochloride.

The present invention therefore also relates to a pharmaceutical composition comprising the crystalline form of Saxagliptin hydrochloride designated as form IV-S, wherein more than 95% of the crystalline form of Saxagliptin hydrochloride, designated as form IV-S present in said composition is stably present as form IV-S, in particular, the present invention relates to such pharmaceutical compositions wherein form IV-S is the only detectable crystalline from of Saxagliptin hydrochloride.

"Stably present" as defined herein means that even after storage of the pharmaceutical composition for 180 days, and preferably even after storage for two years, the crystalline form of Saxagliptin hydrochloride initially comprised in the pharmaceutical composition is still present as crystalline form of Saxagliptin hydrochloride after storage for the indicated period. Such compositions can be produced by avoiding humid conditions, such as high relative humidity of the air, during the formulation steps. Furthermore, the above-identified humid conditions are to be avoided during storage in order to preserve the pharmaceutical composition of the invention.

In a preferred embodiment the pharmaceutical composition of the invention comprises the crystalline form of Saxagliptin hydrochloride designated as form I-S as the only detectable form of Saxagliptin hydrochloride. Analysis of the polymorphic state of Saxagliptin hydrochloride in a pharmaceutical composition can be performed by any suitable method known in the art, for example by XRPD.

Equilibrium Humidity

It is preferred that the pharmaceutical composition of the invention comprising the crystalline form of Saxagliptin hydrochloride designated as form T-S or form HT-IV-S exhibits an equilibrium relative humidity of below 50%, preferably of from 3% to 50%, more preferably of from 10% to 45%, preferably from 15% to 45%, in particular more preferably of from 15% to 40% or from 25% to 35%, for at least 180 days, preferably for at least two years.

It is preferred that the pharmaceutical composition of the invention comprising the crystalline form of Saxagliptin hydrochloride designated as form IV-S exhibits an equilibrium relative humidity of below 40%, preferably of from 3% to 40%, more preferably of from 10% to 40%, preferably from 15% to 40%, in particular more preferably of from 15% to 40% or from 25% to 35%, for at least 180 days, preferably for at least two years.

The equilibrium relative humidity of the pharmaceutical compositions comprising the crystalline form of Saxagliptin hydrochloride is measured by determining the relative humidity in % in the air above a test sample, e.g. a pharmaceutical composition of the invention comprising the crystalline form of Saxagliptin hydrochloride designated as form I-S or form HT-IV-S, after establishment of a humidity equilibrium in a closed system at a constant temperature according to the following method: the equipment used is the commercially available measuring chamber Rotronic AW-VC comprising a hygrometer of the type BT-RS1. The test sample, e.g. a pharmaceutical composition of the invention is filled into a sampling dish which is placed into the measuring chamber which has been thermostated to a temperature of 25+/−1° C., said chamber is subsequently closed and sealed. After establishment of an equilibrium of the relative humidity which state is typically shown by the disappearance of a trend indication, the value of the relative humidity in % is read from the hygrometer. Relative humidity is defined as the equilibrium relative humidity of the pharmaceutical compositions as measured as herein described. Filling of the chamber is to be performed in such a way as to provide complete filling of said chamber according to the instructions of the manufacturers. In case the test sample is a powder or granules for oral suspension, or a liquid suspension, said sample is directly placed into the above mentioned sampling dish. In case the test sample is a capsule, the appropriate number of capsules is opened and their contents is filled into the sampling dish. In case the test sample is a tablet, the appropriate number of tablets is crushed by using a mortar, and filled into the sampling dish. In cases where the equilibrium humidity is expected to be below 20%, the above described preparation of the test samples before measurement and the measurement itself as herein described is to be performed in a glove box being equipped with a hygrometer wherein a relative humidity of about 5% is to be established by e.g. flushing with dried air or nitrogen. The above described method for measurement of the equilibrium relative humidity of the pharmaceutical compositions of the invention is herein also called ERH method.

Storage Conditions

The pharmaceutical composition of the present invention comprising the crystalline form of Saxagliptin hydrochloride designated as form I-S, IV-S or form HT-IV-S is preferably stored in a relatively dry environment, and preferably it is to be assured that the storage environment remains relatively dry during the lifetime of the pharmaceutical composition.

In one preferred embodiment the compounds and compositions especially form I-S and HT-IV-S according to the present invention are stored in a container capable to keep the equilibrium relative humidity of the composition at below 50%, preferably at from 10% to 45%, more preferably at from 15% to 40%, for at least 180 days, more preferably for at least two years. This can be achieved, for example, by use of a tightly sealed container, or by equipping the container with a means to keep the composition relatively dry.

In another preferred embodiment, the invention therefore also relates to a container comprising a pharmaceutical composition of the invention comprising the crystalline form of Saxagliptin hydrochloride designated as form IV-S, which container is capable to keep the equilibrium relative humidity of the composition at below 40%, preferably at from 10% to 40%, more preferably at from 15% to 40%, for at least 180 days, more preferably for at least two years. This can be achieved, for example, by use of a tightly sealed container, or by equipping the container with a means to keep the composition relatively dry.

Such a drying means may be, for example, desiccant bags, e.g. as commercially available under the trade name MINI-PAX and containing 2 g of molecular sieve 4 Angstrom; or desiccant canisters, e.g. as available under the trade name SORBIT and containing 1 g Silicagel; desiccant capsules, e.g. as available under the trade name DRICAP, and containing 0.9 g Silicagel, or desiccant stoppers containing 2 g Silicagel.

Storage Container

The products or intermediate products obtained in the various steps of herein described processes are preferably stored at an environmental relative humidity of below 50%, preferably below 40%. Said products may thus be stored in aluminium barrels or drums, in so-called Nirosta® drums, such as commercially available as Müller® drums. Said drums may be made gas-tight, e.g. air-tight by applying a sealing means, such as sealing rings to the lid thereof. Said products may also be stored in containers made of aluminium or Nirosta®-material as mentioned above whereof the closures or lids are provided with a sealing means, such as a sealing ring.

The pharmaceutical compositions of the invention comprising the crystalline form of Saxagliptin hydrochloride especially designated as form I-S or form HT-IV-S are preferably packaged or filled into containers as herein described at an environmental relative humidity of below 50%, preferably at from 10% to 45%. Subsequently, said containers are tightly closed as herein described. Preferably, said containers are used for stable storage of the pharmaceutical compositions of the invention, for example at room temperature, such as at a temperature of about 20° C. to 30° C., e.g. at about 25° C., for a prolonged period, e.g. for at least 6 months, preferably at least about 24 months, e.g. for up to at least 24 months, e.g. for up to at least about 30 months, such as for up to about 60 months.

The pharmaceutical compositions of the invention comprising the crystalline form of Saxagliptin hydrochloride designated as form IV-S are preferably packaged or filled into containers as herein described at an environmental relative humidity of below 40%, preferably at from 10% to 40%. Subsequently, said containers are tightly closed as herein described. Preferably, said containers are used for stable storage of the pharmaceutical compositions of the invention, for example at room temperature, such as at a temperature of about 20° C. to 30° C., e.g. at about 25° C., for a prolonged period, e.g. for at least 6 months, preferably at least about 24 months, e.g. for up to at least 24 months, e.g. for up to at least about 30 months, such as for up to about 60 months.

A preferred container is a bottle, e.g. a glass or plastic bottle, e.g. a polyethylene bottles, such as known as securitainer, having e.g. a screw closure, or is a blister, e.g. an aluminium blister or strip, e.g. a blister consisting of 2 aluminum foils or strips, or a blister comprising an Aclar® foil and an aluminum cover foil, or may be any other suitable container. More preferably said container is a gas-tight container, such as an air-tight container.

Preferred containers are glass or plastic bottles sealed with an aluminum membrane, alu-alu-blisters or strips, or blisters comprising an Aclar® foil and an aluminum cover foil. The container according to the invention is obtained by filling the pharmaceutical compositions of the invention into said container under the conditions as herein described.

Preferably, the container in combination with the drying means is capable of maintaining the equilibrium relative humidity of the pharmaceutical composition of the invention comprising the crystalline form of Saxagliptin hydrochloride designated as form I-S or form HT-IV-S therein at below 50%, preferably at from 10% to 45%, for at least 6 months, preferably for at least two years. In a preferred embodiment the container further encloses a gaseous atmosphere with a relative humidity of below 50%, preferably of from 10% to 45%. Equipping the container with a dry gaseous atmosphere, for example dry air or dry nitrogen gas, can be performed as known in the art. With regard to form IV-S the container in combination with the drying means is capable of maintaining the equilibrium relative humidity of the pharmaceutical composition at below 40%, preferably at from 10% to 40%, for at least 6 months, preferably for at least two years. In a preferred embodiment the container further encloses a gaseous atmosphere with a relative humidity of below 40%, preferably of from 10% to 40%.

Preferred combinations of container and drying means are aluminum-foil-sealed polyethylene-bottles (PE-bottles) containing desiccant capsules and/or canisters or glass bottles with desiccant stoppers.

Preparation of Compositions

Special care as to the relative environmental humidity and as to the equilibrium relative humidity of the composition has to be taken during the production of pharmaceutical compositions of the invention comprising form I-S, IV-S or form HT-IV-S. Therefore, the present invention also relates to a process for preparing a pharmaceutical composition of the invention comprising the crystalline form of Saxagliptin hydrochloride designated as form I-S, IV-S or form HT-IV-S comprising the steps of a) mixing the crystalline form of Saxagliptin hydrochloride designated as form I-S or form HT-IV-S with one or more pharmaceutically acceptable excipients at a relative humidity of below 50%, preferably at from 10% to 45% and as regards form IV-S at a relative humidity of below 40%, preferably at from 10 to 40%;
b) optionally granulating the mixture obtained in step a) at a relative humidity of below 50%, preferably at from 10% to 45% as regards form I-S and HT-IV-S and at a relative humidity of below 50%, preferably at from 10% to 40% as regards form IV-S; and
c) further processing the mixture obtained in step a) or the granulate obtained in step b) at a relative humidity of below 50%, preferably at from 10% to 45% as regards form I-S and HT-IV-S and at a relative humidity of below 40%, preferably at from 10% to 40% as regards form IV-S, to obtain a pharmaceutical composition of the invention comprising the crystalline form of Saxagliptin hydrochloride designated as form I-S or as form HT-IV-S or as form IV-S.

It is preferred that the obtained pharmaceutical composition of the invention exhibits an equilibrium relative humidity of below 50%, preferably of from 10% to 45%, more preferably of from 15% to 30% or of from 20% to 45% as regards form I-S and HT-IV-S and an equilibrium relative humidity of below 40%, preferably of from 10 to 40%, more preferably of from 15 to 30% as regards form IV-S.

The mixture obtained from step a) or the granulate obtained from step b) as described above is preferably processed into an oral dosage form, like a capsule or a tablet, or granules for oral suspension, or a powder for oral suspension.

In a preferred embodiment, the obtained pharmaceutical composition comprising the crystalline form of Saxagliptin hydrochloride designated as form I-S or form HT-IV-S having an equilibrium relative humidity of below about 50%, preferably of from 10% to 45%, is filled into a container capable of maintaining the equilibrium relative humidity of the pharmaceutical composition at below 50%, preferably at from 10% to 45%, for at least 6 months, for examples the containers mentioned above, which may optionally further comprise a drying means sufficient to maintain the equilibrium relative humidity of the pharmaceutical composition at below 50%, preferably at from 10% to 45%.

The proper storage conditions for the pharmaceutical compositions of the invention comprising the crystalline form of Saxagliptin hydrochloride designated as form I-S or form HT-IV-S are important for maintaining the compositions in the desired form. Thus, preferably a container is used capable of maintaining a gaseous atmosphere at a relative humidity of below 50%, preferably at from 10% to 45%, for at least 6 months for storage of a pharmaceutical composition of the invention. Preferably, a gaseous atmosphere having a relative humidity of below 50%, preferably at from 10% to 45%, is used to stabilize the crystalline form of Saxagliptin hydrochloride designated as form I-S or form HT-IV-S and a relative humidity of below 40%, preferably at from 10% to 40% as regards form IV-S.

After the pharmaceutical compositions of the invention have been filled into the herein mentioned containers, said containers are preferably tightly closed, e.g. tightly or hermetically sealed, e.g. in a way to prevent any gaseous atmosphere from diffusing through the walls and/or closure of said containers. Methods of tightly sealing and/or closing said containers are known, such as sealing of glass or plastic bottles by applying an aluminium membrane to the bottle opening of said bottle by induction sealing and by applying a closure, e.g. a screw closure, or such as sealing of alu-alu blisters or strips, of blisters comprising an Aclar® foil and an aluminium cover foil by heat sealing according, e.g. analogously to known methods.

The temperature applied during the herein described processes is preferably room temperature, e.g. is a temperature of about 20° C. to about 30° C., such as about 25° C.

EXAMPLES

X-ray powder diffraction patterns (XRPD) were obtained with a PANalytical X'Pert PRO diffractometer equipped with a theta/theta coupled goniometer in transmission geometry, Cu—K$\alpha_{1,2}$ radiation (wavelength 0.15419 nm) with a focusing mirror and a solid state PIXcel detector. The patterns were recorded at a tube voltage of 40 kV, tube current of 40 mA, applying a stepsize of 0.006° 2θ with 80 s per step in the angular range of 2° to 40° 2θ at ambient conditions. A typical precision of the 2-theta values is in the range of about ±0.2° 2-theta. Thus a diffraction peak that appears at 5.0° 2-theta can appear between 4.8 and 5.2° 2-theta on most X-ray diffractometers under standard conditions.

Infrared spectra (IR) were collected on a MKII Golden Gate™ Single Reflection Diamond ATR (attenuated total reflection) cell with a Bruker Tensor 27 FTIR spectrometer with 4 $cm^{-1}$ resolution. To collect a spectrum a spatula tip of a sample was applied to the surface of the diamond in powder form. Then the sample was pressed onto the diamond with a sapphire anvil and the spectrum was recorded. A spectrum of the clean diamond was used as background spectrum. A typical precision of the wavenumber values is in the range of about ±2 $cm^{-1}$. Thus, an infrared peak that appears at 1716 $cm^{-1}$ can appear between 1714 and 1718 $cm^{-1}$ on most infrared spectrometers under standard conditions.

Differential scanning calorimetry (DSC) was performed with a DSC 7 (Perkin-Elmer, Norwalk, Conn., USA) using the Pyris software. A sample of about 4 mg was weighed into a 25 μl Al-pan. Dry nitrogen was used as the purge gas (purge: 20 ml $min^{-1}$). When used herein, the term "$T_{onset}$" determined by Differential Scanning calorimetry means the temperature corresponding to the intersection of the pretransition baseline with the extrapolated leading edge of the transition.

Thermogravimetric analysis was performed with the thermogravimetric system TGA-7 using the Pyris Software for Windows NT (Perkin-Elmer, Norwalk, Conn., USA), 50 μl platinum pans, nitrogen purge gas (sample purge: 20 ml $min^{-1}$, balance purge: 40 ml $min^{-1}$).

The moisture sorption isotherm was recorded with a SPS-11 moisture sorption analyzer (MD Mess-technik, Ulm, D). The measurement cycle was started at 0% relative humidity (RH), increased in 10% steps up to 90% RH and in a 5% step up to 95% RH. The equilibrium condition for each step was set to a constant mass±0.003% over 49 min. The temperature was 25±0.1° C.

HPLC assay was performed by applying the following conditions:
Column: YMC-Ultra HT Pro C 18 3.0×50.0 mm, 2 µm
Eluent A: 10 mM Sulfamic acid
Eluent B: 250 ml 10 mM SAS+750 ml acetonitril
Flow rate: 0.64 mL/min
Temperature: 15° C.
Detection: UV at 210 nm
Gradient:

| t [min] | 0 | 10 | 12 | 12.1 | 15 |
|---|---|---|---|---|---|
| % B | 0 | 70 | 70 | 0 | 0 |

Stop time: 15 min
Sample concentration: about 0.5 mg/ml
Solvent: Eluent A
Injection Vol: 5 µl Example 1

Preparation of Anhydrous Form 1-S of Saxagliptin Monohydrochloride 4.58 g Saxagliptin free base hemihydrate were dissolved in 230 ml acetone. To this solution 2.2 ml Trimethylchlorosilane were added under stirring. After one hour the mixture containing a gelatinous precipitate was evaporated. To the solid residue 80 ml ethanol was added and the slurry was stirred in an open flask for about one hour. The product was filtered off, washed with tert.-Butyl methyl ether and then dried in a vacuum oven to give 1.65 g Saxagliptin Monohydrochloride Dihydrate. Polymorphism of Saxagliptin Monohydrochloride Dihydrate was determined by X-ray diffraction, FT-IR and DSC.

The mother liquor was put into a refrigerator at −5° C. for 48 hours. Surprisingly, additional crystals had formed from the mother liquor. The so obtained crystalline precipitate was filtered off, washed with tert.-Butyl methyl ether and then dried in a vacuum oven. The crystals were analyzed and found to be 1.22 g Saxagliptin Monohydrochloride. The obtained product from the mother liquor was found to be a new anhydrous polymorphic form of Saxagliptin Monohydrochloride, denominated as form I-S.
purity by HPLC: 99.7 area % (max individual impurity 0.09%, total impurities 0.33%)

Figure 1:
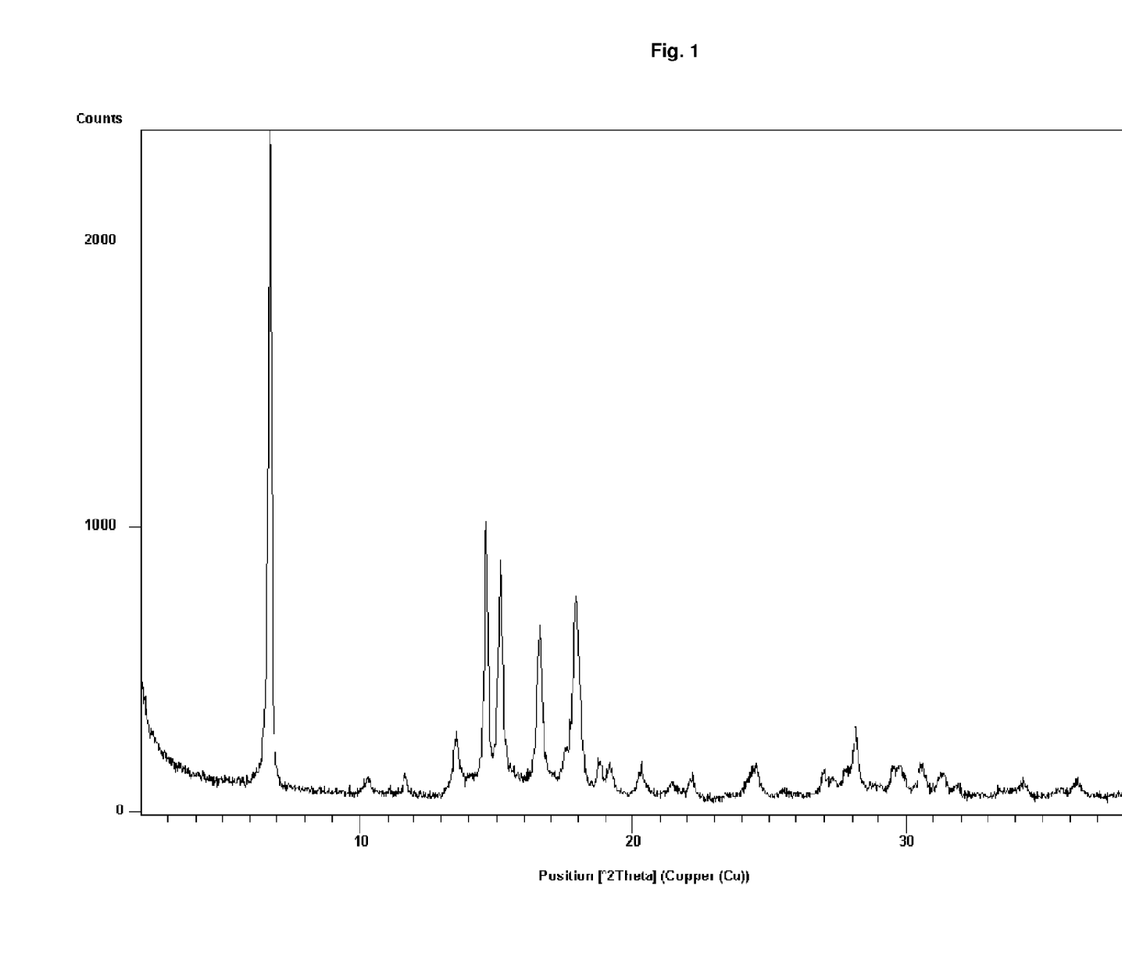
FIG. 1: PXRD pattern of Saxagliptin Hydrochloride form I-S

The powder X-ray diffraction pattern of Saxagliptin Monohydrochloride form I-S is shown in FIG. 1. Characteristic XRPD angles, d-spacings and relative intensities are shown in Table 1.

TABLE 1

Angles 2-theta, d-values and relative intensities of form I-S

| Angle [2-Theta °] | d value [Angstrom] | rel. Int. [%] |
|---|---|---|
| 6.72 | 13.145 | 100 |
| 10.30 | 8.591 | 4 |
| 11.68 | 7.577 | 3 |
| 13.52 | 6.548 | 12 |
| 14.63 | 6.054 | 46 |
| 15.15 | 5.846 | 36 |
| 16.60 | 5.340 | 32 |
| 17.91 | 4.952 | 53 |
| 18.80 | 4.721 | 7 |
| 19.19 | 4.624 | 7 |
| 20.33 | 4.368 | 4 |
| 21.46 | 4.141 | 4 |
| 22.17 | 4.010 | 5 |
| 24.50 | 3.634 | 17 |
| 27.01 | 3.301 | 6 |
| 28.16 | 3.169 | 12 |
| 29.78 | 3.001 | 9 |
| 30.59 | 2.922 | 9 |
| 31.33 | 2.855 | 9 |
| 31.87 | 2.808 | 3 |
| 34.27 | 2.616 | 4 |
| 36.25 | 2.478 | 5 |

Figure 2:
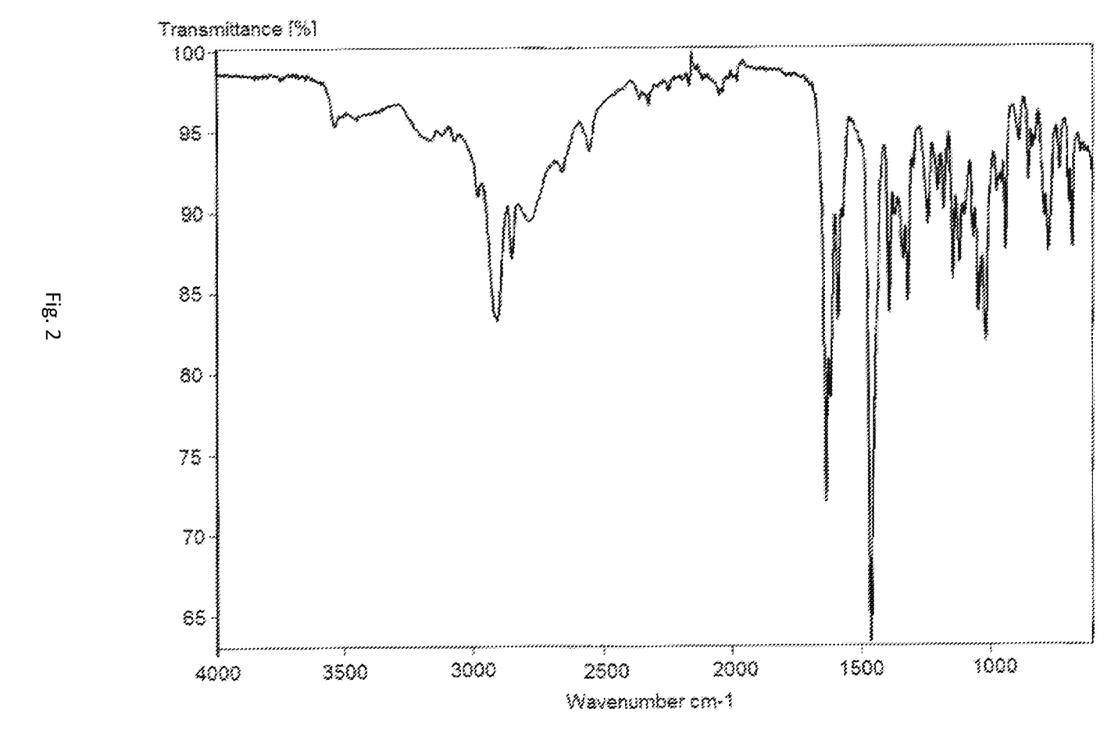
FIG. 2: FTIR spectrum of Saxagliptin Hydrochloride form I-S

Crystalline form I-S of Saxagliptin Monohydrochloride obtained above has an attenuated total reflectance IR spectrum with absorption bands at 2907, 2853, 1637, 1589, 1462, 1391, 1318, 1045, 1014 and 775 cm$^{-1}$ (±2 cm$^{-1}$; FIG. 2)

Figure 3:
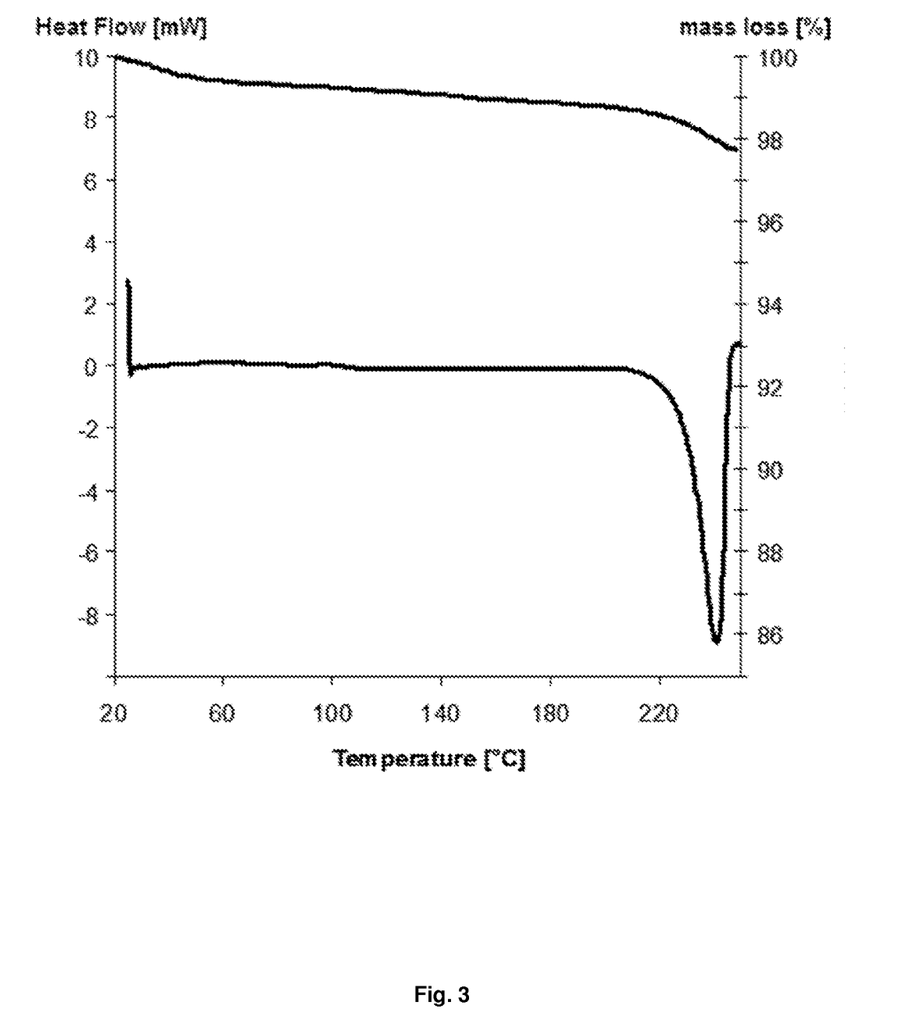
FIG. 3: DSC of Saxagliptin Hydrochloride form I-S

The obtained crystalline form I-S was subjected to differential thermal analysis. As can be seen in FIG. 3 (lower curve), crystalline form I-S shows no significant dehydration endotherm but only a peak at 241° C. ($T_{onset}$ 230° C.; heating rate 10° C./minute, pinholed capsule).

Ionic chlorine was determined as 10.7% (theory 10.08%)

The water content of the obtained crystalline form I-S was determined as 1.2% w/w using a Karl Fischer apparatus. At about 50% relative humidity at 25° C. form 1 S of Saxagliptin Hydrochloride shows a water content of about 1.5%. This water is lost completely when lowering the relative humidity at 25° C. to about 0.5%. The process is reversible when exposing Saxagliptin hydrochloride to a humidity of about 50%.

Form I-S is stable below 50% relative humidity. Above about 50% relative humidity Form I-S transforms to the known Dihydrate H2-1. This transformation is not reversible.

Example 2

Preparation of Anhydrous Form I-S of Saxagliptin Monohydrochloride from Ethanol by Seeding 2.31 g Saxagliptin Monohydrochloride was suspended in 62 ml ethanol and the resultant mixture was heated at reflux. The hot solution was filtered, then seeded with the product of example 1. The mixture was cooled to 25° C. and then put into a refrigerator over night. The white solid was collected by filtration and dried in a vacuum oven to give 0.78 g of Saxagliptin Monohydrochloride form I-S.

Example 3

Preparation of Form HT-S of Saxagliptin Monohydrochloride 10 mg Saxagliptin Monohydrochloride Dihydrate was heated up to 180° C. with 10° K/min under Nitrogen. Form HT-S was obtained.

Figure 4:
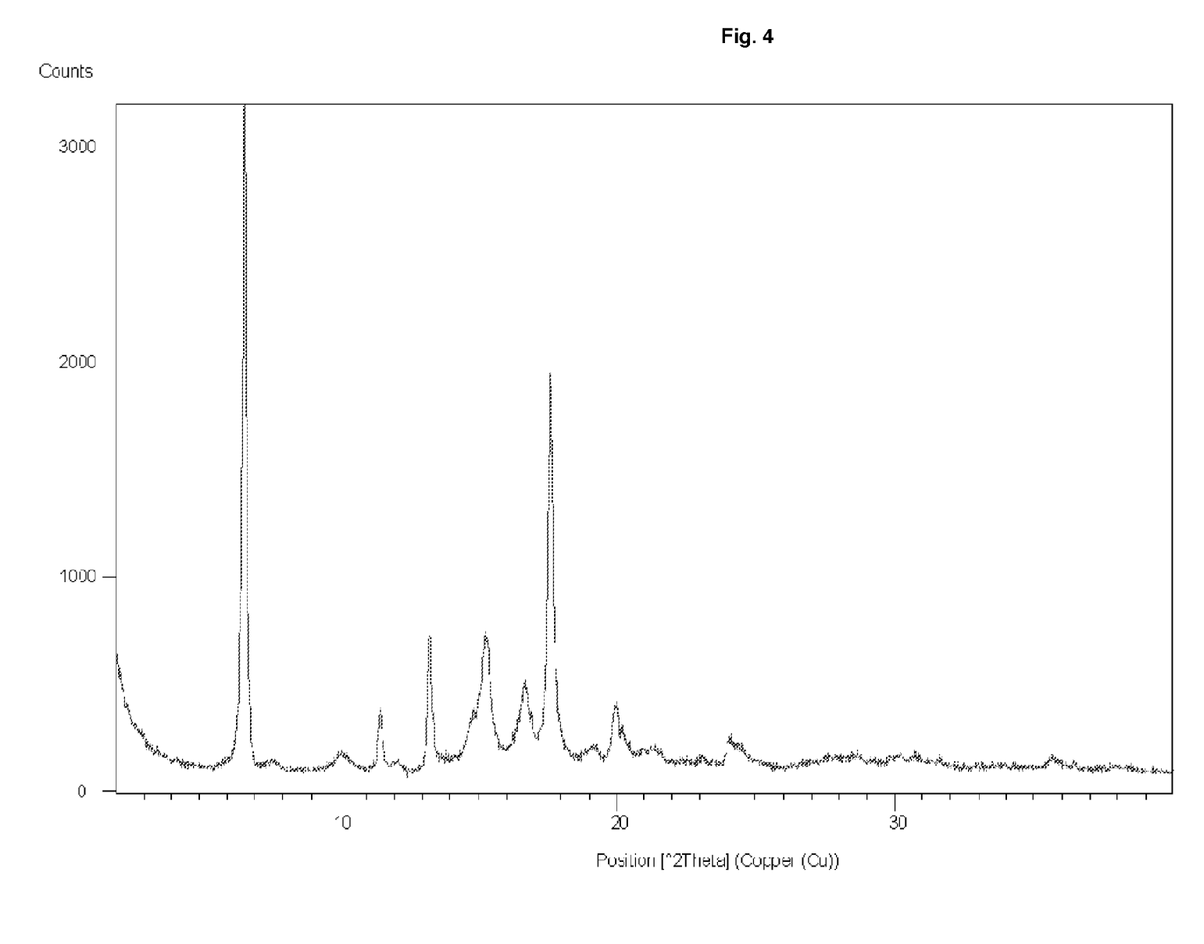
FIG. 4: PXRD pattern of Saxagliptin Hydrochloride form HT-S

The powder X-ray diffraction pattern of Saxagliptin Monohydrochloride form HT-S is shown in FIG. 4. Characteristic XRPD angles, d-spacings and relative intensities are shown in Table 2.

TABLE 2

Angles 2-theta, d-values and relative intensities of form HT-S

| Angle [2-Theta °] | d value [Angstrom] | rel. Int. [%] |
|---|---|---|
| 6.62 | 13.357 | 100 |
| 7.63 | 11.591 | 3 |
| 10.11 | 8.749 | 7 |
| 11.48 | 7.707 | 7 |
| 12.08 | 7.326 | 3 |
| 13.27 | 6.673 | 14 |
| 15.28 | 5.799 | 40 |
| 16.69 | 5.313 | 18 |
| 17.60 | 5.039 | 35 |
| 19.15 | 4.635 | 8 |
| 19.97 | 4.446 | 14 |
| 21.32 | 4.168 | 9 |
| 24.11 | 3.691 | 9 |

Figure 5:
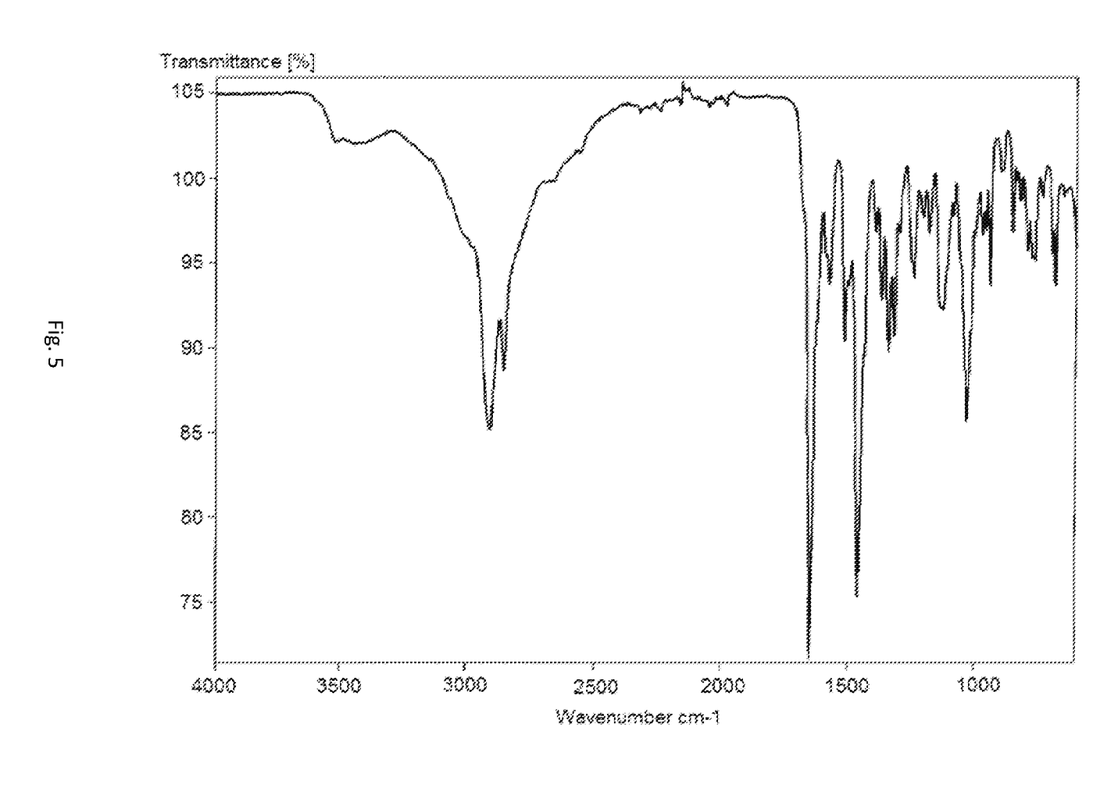
FIG. 5: FTIR spectrum of Saxagliptin Hydrochloride form HT-S

Crystalline form HT-S of Saxagliptin Monohydrochloride obtained above has an attenuated total reflectance IR spectrum with absorption bands at 2906, 2854, 1649, 1574, 1513, 1459, 1338, 1124, 1032 and 851 cm$^{-1}$ (±2 cm$^{-1}$; FIG. 5)

The obtained crystalline form HT-S was subjected to differential thermal analysis. As can be seen in FIG. 3 (lower curve), crystalline form HT-S shows no significant dehydration endotherm but only a peak at 230° C. (heating rate 10° C./minute, pinholed capsule).

Figure 6:
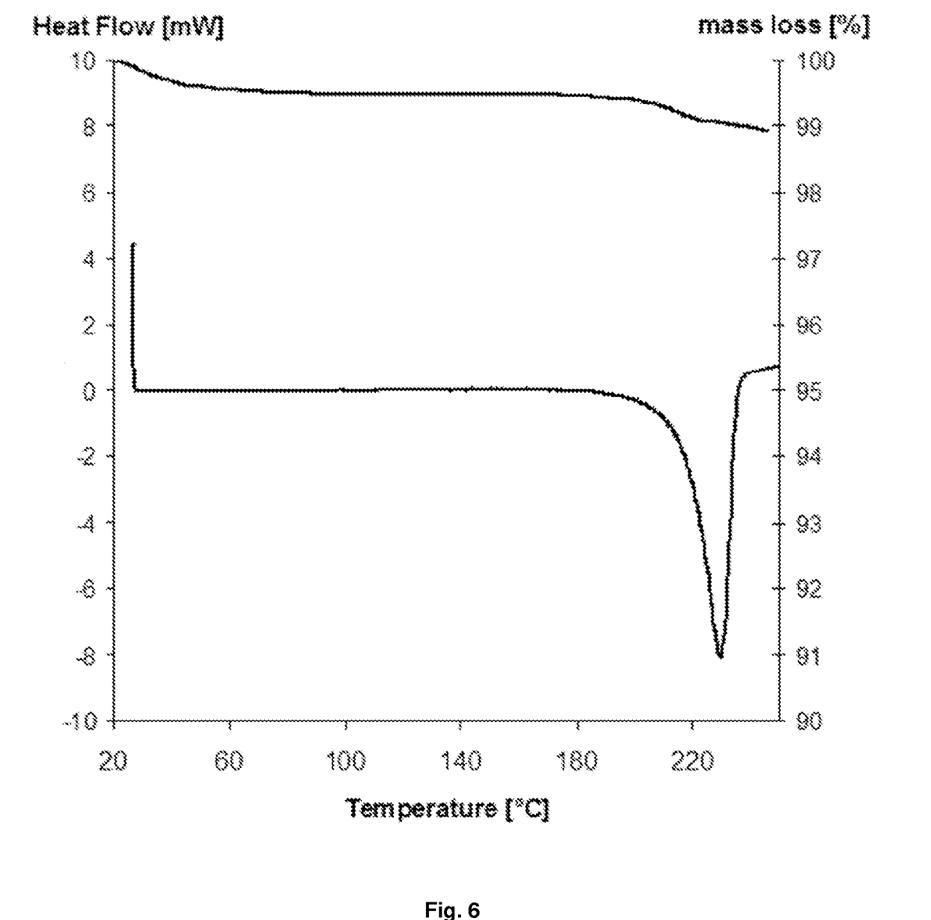
FIG. 6: DSC of Saxagliptin Hydrochloride form HT-S

The obtained crystalline form HT-S showed a water loss of not more than 0.5% w/w based on thermogravimetric analysis (FIG. 6, upper line).

Example 4

Preparation of Form HT-IV-S

Step 1, Preparation of Form IV-S 105 mg of Saxagliptin Monohydrochloride dihydrate form H2-1 were dissolved in 11 ml of n butanole. The solution obtained was filtered and the solvent was removed by vacuo at approximately 20 mbar using a rotavap. To the residue 4 ml of tert. amylalkohol were added and a suspension was obtained. The suspension was stirred for 3 days and the crystals were than isolated by suction and kept in a dessicator at about 30% relative humidity overnight.

Yield: 97 mg Saxagliptin Hydrochloride form IV-S

Step 2, Preparation of Form HT-IV-S

The crystalline product Saxagliptin Hydrochloride IV-S was dried in a vacuum oven at 50° C. for approximately 10 hours at a vacuum of about 40° C. followed by drying at about 80° C. for 5 hours to yield crystalline form HT-IV S Water (KF): 0.7%

A sample was stored at 45-49% relative humidity for 12 hours.

Water (KF): 1.2%

No change in the crystal form was observed (FTIR).

Figure 7:
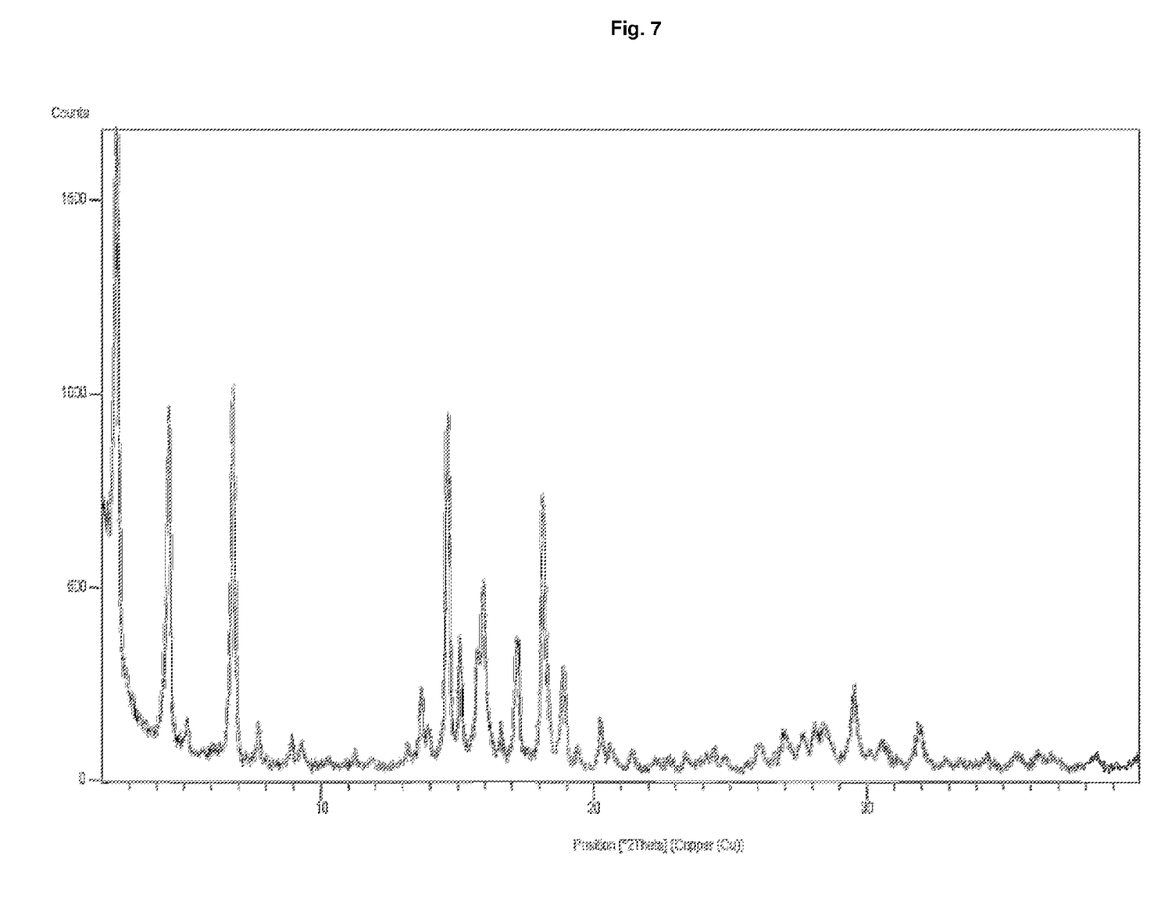
FIG. 7: PXRD pattern of Saxagliptin Hydrochloride form HT-IV-S

The powder X-ray diffraction pattern of Saxagliptin Monohydrochloride form HT-IV S is shown in FIG. 7. Characteristic XRPD angles, d-spacings and relative intensities are shown in Table 3.

TABLE 3 angles 2-theta, d-values and relative intensities of form HT-IV-S

| Angle [2-Theta °] | d value [Angstrom] | rel. Int. [%] |
|---|---|---|
| 2.56 | 34.561 | 100 |
| 4.46 | 19.832 | 69 |
| 5.14 | 17.191 | 6 |
| 6.82 | 12.965 | 74 |
| 7.73 | 11.433 | 7 |
| 8.94 | 9.889 | 6 |
| 13.69 | 6.47 | 15 |
| 13.93 | 6.357 | 6 |
| 14.64 | 6.05 | 70 |
| 15.1 | 5.866 | 23 |
| 15.77 | 5.618 | 20 |
| 15.97 | 5.551 | 35 |
| 16.6 | 5.342 | 6 |
| 17.19 | 5.158 | 23 |
| 18.14 | 4.89 | 54 |
| 18.88 | 4.7 | 17 |
| 20.27 | 4.381 | 9 |
| 26.99 | 3.304 | 6 |
| 27.67 | 3.223 | 5 |
| 28.11 | 3.175 | 7 |
| 28.47 | 3.135 | 7 |
| 29.53 | 3.026 | 13 |
| 31.92 | 2.804 | 7 |

Figure 8:
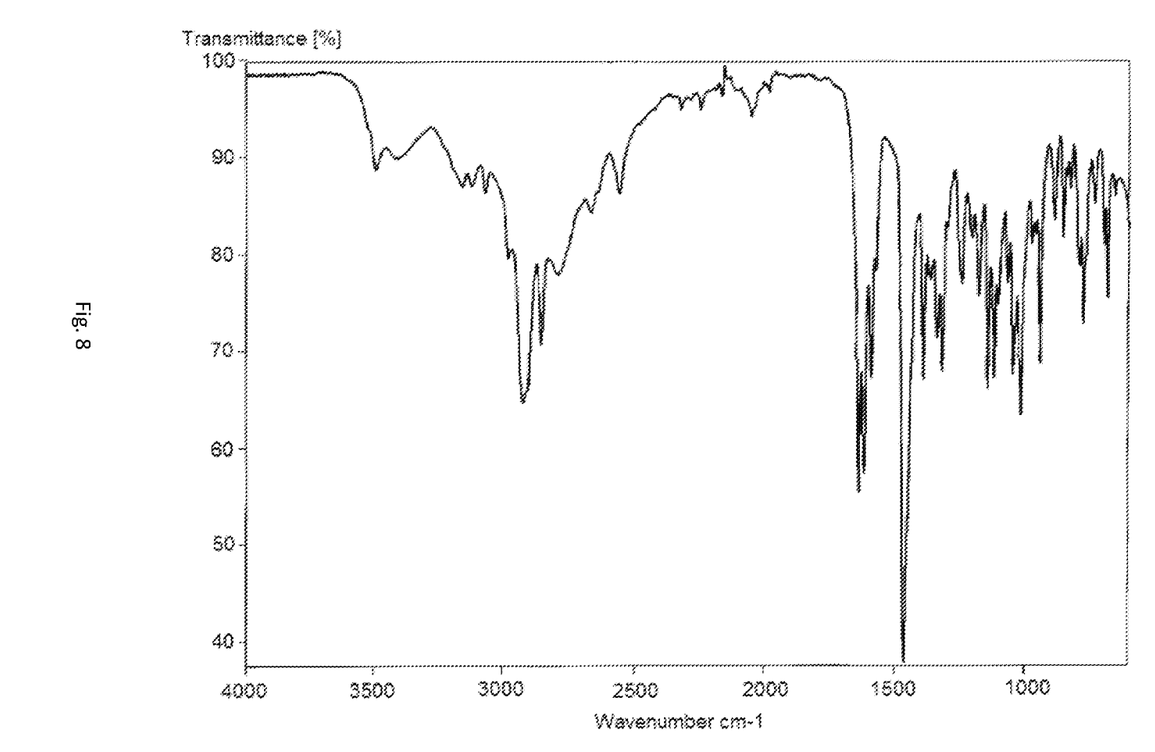
FIG. 8: FTIR spectrum of Saxagliptin Hydrochloride form HT-IV-S

Crystalline form HT-IV-S of Saxagliptin hydrochloride obtained above has an attenuated total reflectance IR spectrum with absorption bands at wavenumbers of 3495, 2921, 1637, 1616, 1464, 1242, 1103, 1013, 940 and 774 (±2 cm$^{-1}$; FIG. 8).

Figure 9:
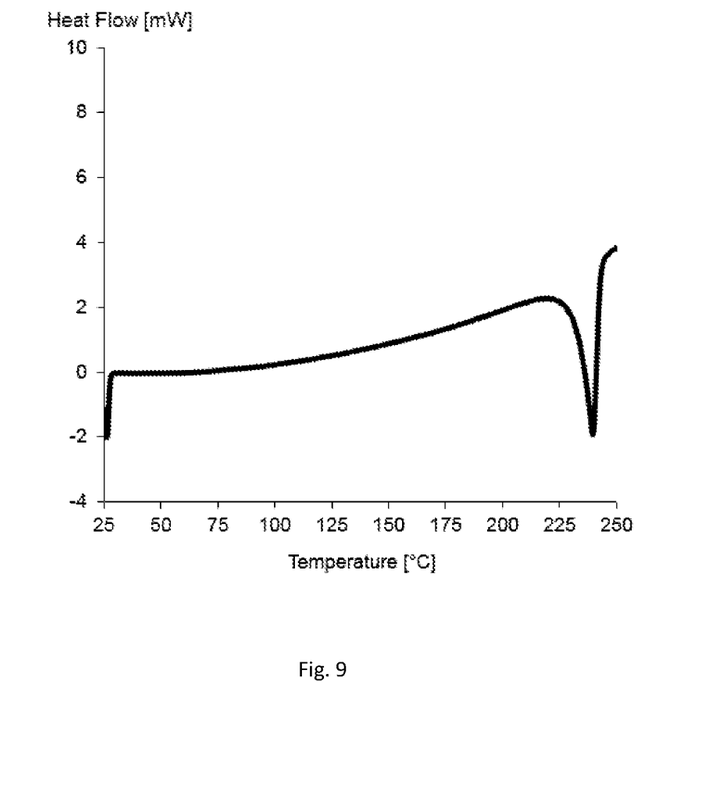
FIG. 9: DSC of Saxagliptin Hydrochloride form HT-IV-S

The obtained crystalline form HT-IV-S was subjected to differential thermal analysis. As can be seen in FIG. 9, crystalline form HT-IV-s shows no significant dehydration endotherm but only a peak at 240° C. (T$_{onset}$ 232° C. (heating rate 10° C./minuter, pinholed capsule).

Example 5

Preparation of Form IV-S of Saxagliptin Monohydrochloride 105 mg of Saxagliptin Monohydrochloride dihydrate form H2-1 were dissolved in 11 ml of n butanole. The solution obtained was filtered and the solvent was removed by vacuo at approximately 20 mbar using a rotavap. To the residue 4 ml of tert. amylalkohol were added and a suspension was obtained. The suspension was stirred for 3 days and the crystals were than isolated by suction and kept in a dessicator at about 30% relative humidity overnight.

Yield: 97 mg

Figure 10:
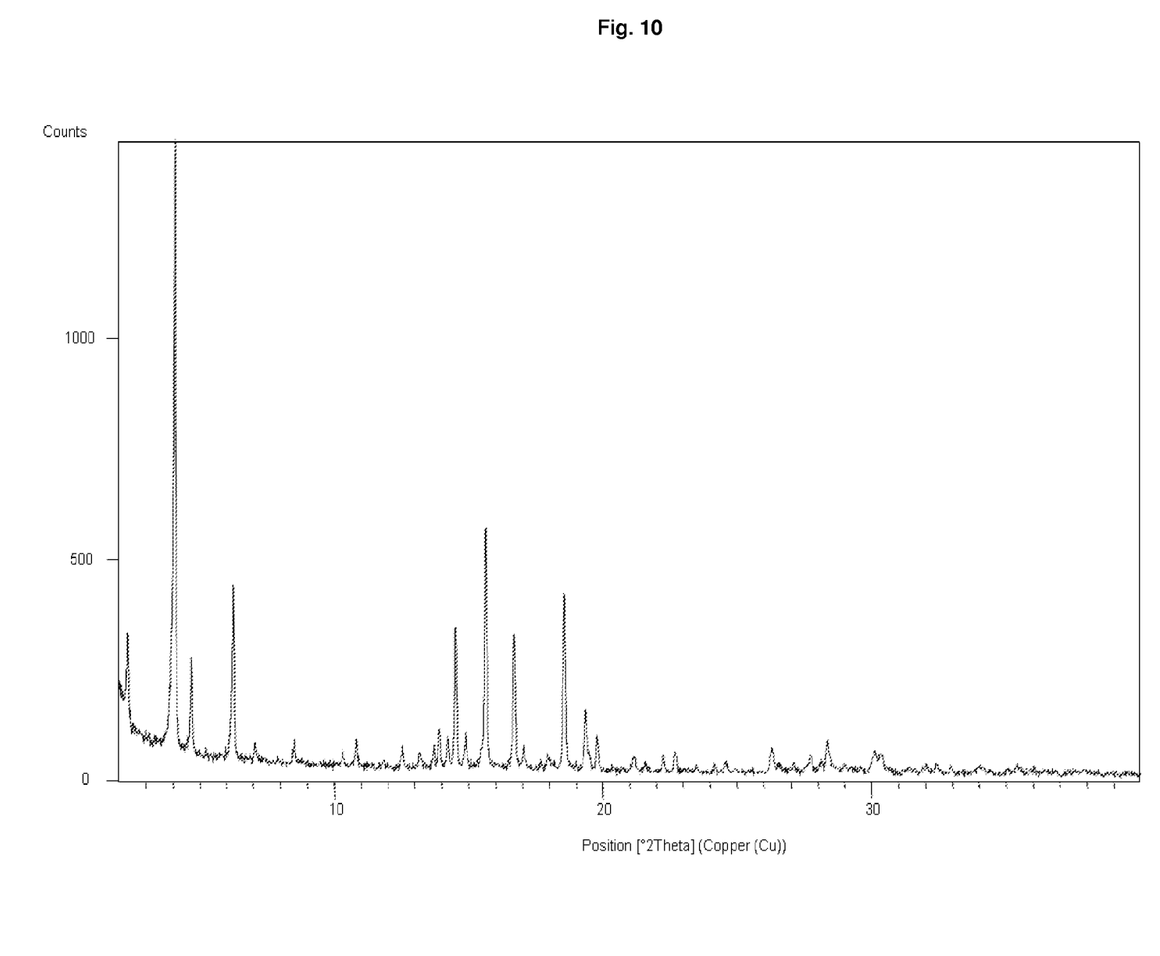
FIG. 10: PXRD pattern of Saxagliptin Hydrochloride form TV-S

The powder X-ray diffraction pattern of Saxagliptin Monohydrochloride form IV-S is shown in FIG. 10. Characteristic XRPD angles, d-spacings and relative intensities are shown in Table 4.

TABLE 4

Angles 2-theta, d-values and relative intensities of form IV-S

| Angle [2-Theta °] | d value [Angstrom] | rel. Int. [%] |
|---|---|---|
| 2.35 | 37.566 | 14 |
| 4.08 | 21.652 | 100 |
| 4.72 | 18.738 | 15 |
| 6.25 | 14.143 | 29 |
| 13.91 | 6.368 | 6 |

TABLE 4-continued

Angles 2-theta, d-values and relative intensities of form IV-S

| Angle<br>[2-Theta °] | d value<br>[Angstrom] | rel. Int.<br>[%] |
|---|---|---|
| 14.51 | 6.104 | 23 |
| 14.89 | 5.948 | 5 |
| 15.64 | 5.667 | 39 |
| 16.69 | 5.312 | 22 |
| 18.55 | 4.784 | 29 |
| 19.37 | 4.582 | 10 |
| 19.8 | 4.484 | 6 |

Figure 11:
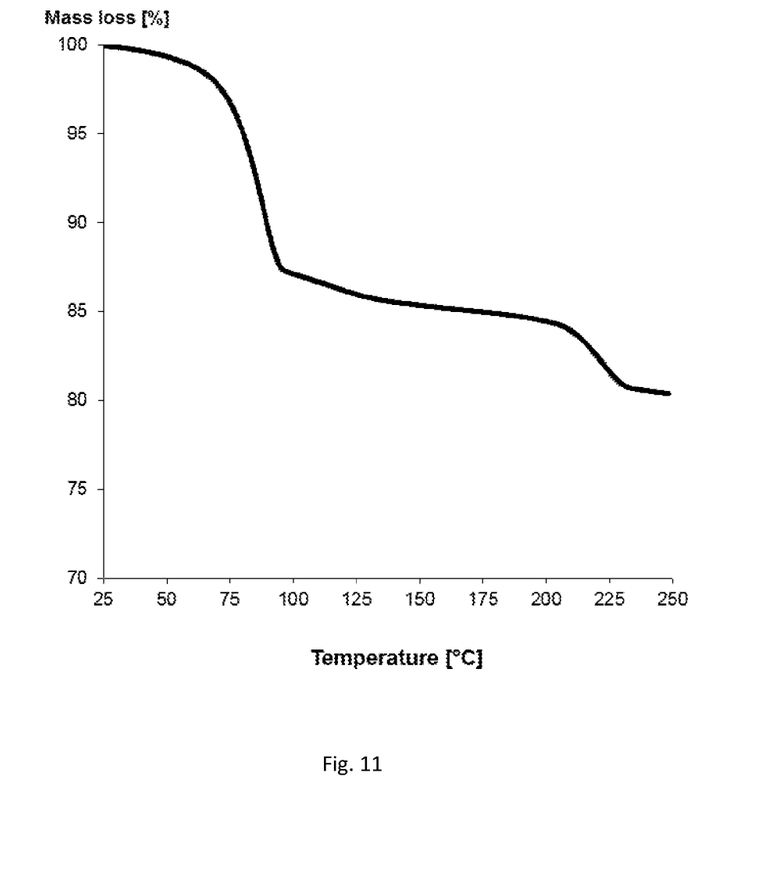
FIG. 11: TGA of Saxagliptin Hydrochloride form IV-S

The obtained crystalline form IV-S was subjected to thermogravimetric analysis. As can be seen in FIG. 11 crystalline form IV-S shows a mass loss of about 12.8% starting up to 100° C. This mass loss corresponds to 2.86 mol of water.

Moisture sorption analysis shows a water content of 13.1% at 40% relative humidity at 25° C. corresponding to 2.94 mol of water. Moisture sorption analysis shows a water content of 12.8% corresponding to 2.86% relative humidity at 0% relative humidity. The process is reversible.

At above 40% relative humidity form IV-S irreversible transforms to known form Dihydrate H2-1.

The invention claimed is:

1. Crystalline Form I-S of Saxagliptin hydrochloride having a water content of not more than 1.5% w/w and a x-ray powder diffraction pattern comprising peaks at 6.7±0.2, 14.6±0.2, 15.2±0.2, 16.6±0.2 and 17.9±0.2 degrees two-theta and/or having an infrared spectrum comprising peaks at wavenumbers of 2907, 2853, 1637, 1589, 1462, 1391, 1318, 1045, 1014 and 775+/−2 cm-1, wherein the crystalline form is greater than 95% by weight.

2. Pharmaceutical composition comprising an crystalline form of Saxagliptin according to claim 1 in an effective amount.

3. A process for the preparation of crystalline Saxagliptin hydrochloride Form I-S according to claim 1 comprising the step of allowing Saxagliptin hydrochloride to crystallize from an alcohol in the presence of seed crystals of Saxagliptin hydrochloride Form I-S.

4. A method of treating diabetes and/or related diseases comprising administering to a patient a therapeutically effective amount of crystalline Saxagliptin hydrochloride according to claim 3 alone or in combination with one or more types of antidiabetic agents and/or one or more other types of therapeutic agents which may be administered orally or by injection.

5. A pharmaceutical composition comprising crystalline Saxagliptin hydrochloride according to claim 1, wherein the equilibrium relative humidity of the composition is below 50%.

6. The pharmaceutical composition of claim 5, wherein the equilibrium relative humidity of the composition is from 10% to 40%.

7. The crystalline Form I-S of Saxagliptin hydrochloride according to claim 1 having a x-ray powder diffraction pattern comprising peaks at 24.5±0.2 and 28.2±0.2 degrees two-theta.

8. The pharmaceutical composition according to claim 2, formulated for use in treating diabetes and/or related diseases.

* * * * *